US011890067B2

(12) United States Patent
Bailey et al.

(10) Patent No.: US 11,890,067 B2
(45) Date of Patent: Feb. 6, 2024

(54) POSITIONING ARM FOR A SURGICAL NAVIGATION SYSTEM

(71) Applicant: Synaptive Medical Inc., Toronto (CA)

(72) Inventors: Brent Andrew Bailey, Toronto (CA); Trevor James Dell, Toronto (CA); Bart Verzijlenberg, Toronto (CA); Adam Philip, Toronto (CA); Sean Dowling, Toronto (CA); Robert Lucas, Toronto (CA)

(73) Assignee: SYNAPTIVE MEDICAL INC., Toronto (CA)

( * ) Notice: Subject to any disclaimer, the term of this patent is extended or adjusted under 35 U.S.C. 154(b) by 354 days.

(21) Appl. No.: 17/155,424

(22) Filed: Jan. 22, 2021

(65) Prior Publication Data
US 2021/0137616 A1 May 13, 2021

Related U.S. Application Data

(63) Continuation of application No. 16/114,323, filed on Aug. 28, 2018, now Pat. No. 10,898,282.

(30) Foreign Application Priority Data

Aug. 28, 2017 (CA) .................. CA 2977489

(51) Int. Cl.
A61B 34/30 (2016.01)
B25J 9/02 (2006.01)
(Continued)

(52) U.S. Cl.
CPC .............. A61B 34/30 (2016.02); A61B 17/29 (2013.01); A61B 18/1442 (2013.01);
(Continued)

(58) Field of Classification Search
CPC ....... A61B 34/30; B25J 9/1633; B25J 13/088; B25J 18/007
See application file for complete search history.

(56) References Cited

U.S. PATENT DOCUMENTS 5,345,334 A  9/1994 Heller
5,789,890 A  8/1998 Genov et al.
(Continued)

FOREIGN PATENT DOCUMENTS

CN  101484086 A  7/2009
CN  104736097 A  6/2015
(Continued)

OTHER PUBLICATIONS

Search Report issued by the Intellectual Property Office of China in relation to the corresponding CN107072729A dated Feb. 27, 2023, 3 pages.

Primary Examiner — Nicholas Kiswanto

(57) ABSTRACT

A motion-assisted positioning arm for a medical procedure. The positioning arm includes a base, an arm coupled to the base, and an end effector coupled to the arm. The arm includes a plurality of arm segments. The arm includes a plurality of joints for connecting the arm segments. The end effector may be manipulable with six degrees of freedom in a task-coordinate space based on motion by at least one joint in the plurality of joints. The positioning arm includes a processor to: detect manipulation of and determine forces or torques acting on the end effector; determine a surgical mode for constraining movement of the end effector in the task-coordinate space; determine an end effector velocity based on the determined forces or torques and the surgical mode for moving end effector; and apply at least one joint space movement based on the end effector velocity.

20 Claims, 12 Drawing Sheets

(51) Int. Cl.

| | |
|---|---|
| *A61B 17/29* | (2006.01) |
| *A61B 18/14* | (2006.01) |
| *B25J 13/08* | (2006.01) |
| *B25J 9/16* | (2006.01) |
| *B25J 18/00* | (2006.01) |
| *A61B 34/20* | (2016.01) |
| *F16M 11/06* | (2006.01) |
| *A61B 90/00* | (2016.01) |
| *A61B 34/10* | (2016.01) |
| *A61B 34/00* | (2016.01) |
| *A61B 17/32* | (2006.01) |

(52) U.S. Cl.
CPC ............... *A61B 34/20* (2016.02); *B25J 9/02* (2013.01); *B25J 9/1633* (2013.01); *B25J 13/085* (2013.01); *B25J 13/088* (2013.01); *B25J 18/007* (2013.01); *A61B 17/32* (2013.01); *A61B 34/10* (2016.02); *A61B 34/25* (2016.02); *A61B 90/361* (2016.02); *A61B 2017/2912* (2013.01); *A61B 2034/2055* (2016.02); *A61B 2090/064* (2016.02); *A61B 2090/065* (2016.02); *A61B 2090/066* (2016.02); *A61B 2090/374* (2016.02); *A61B 2090/3735* (2016.02); *A61B 2090/3762* (2016.02); *F16M 11/06* (2013.01)

(56) References Cited

U.S. PATENT DOCUMENTS

| | | | |
|---|---|---|---|
| 6,063,098 | A | 5/2000 | Houser et al. |
| 6,331,181 | B1 | 12/2001 | Tierney et al. |
| 8,167,872 | B2 * | 5/2012 | Schena ............... A61B 34/37 606/1 |
| 8,428,781 | B2 | 4/2013 | Change et al. |
| 8,543,239 | B2 | 9/2013 | Oga et al. |
| 9,795,446 | B2 * | 10/2017 | DiMaio ............... A61B 34/10 |
| 2006/0206284 | A1 * | 9/2006 | Hirabayashi ......... B25J 9/1633 702/141 |
| 2007/0013336 | A1 | 1/2007 | Newlin et al. |
| 2007/0156157 | A1 | 7/2007 | Nahum et al. |
| 2009/0024142 | A1 | 1/2009 | Morales |
| 2009/0062813 | A1 | 3/2009 | Prisco et al. |
| 2010/0198402 | A1 * | 8/2010 | Greer .................. B25J 3/04 901/41 |
| 2013/0282022 | A1 * | 10/2013 | Yousef ................ A61B 90/11 606/130 |
| 2015/0100066 | A1 | 4/2015 | Kostrzewski et al. |
| 2015/0290798 | A1 | 10/2015 | Iwatake |
| 2015/0359597 | A1 | 12/2015 | Gombert et al. |
| 2017/0274523 | A1 | 9/2017 | Sato |

FOREIGN PATENT DOCUMENTS

| | | |
|---|---|---|
| CN | 106456265 A | 2/2017 |
| CN | 107072729 A | 8/2017 |
| JP | 2009291363 A | 12/2009 |

\* cited by examiner

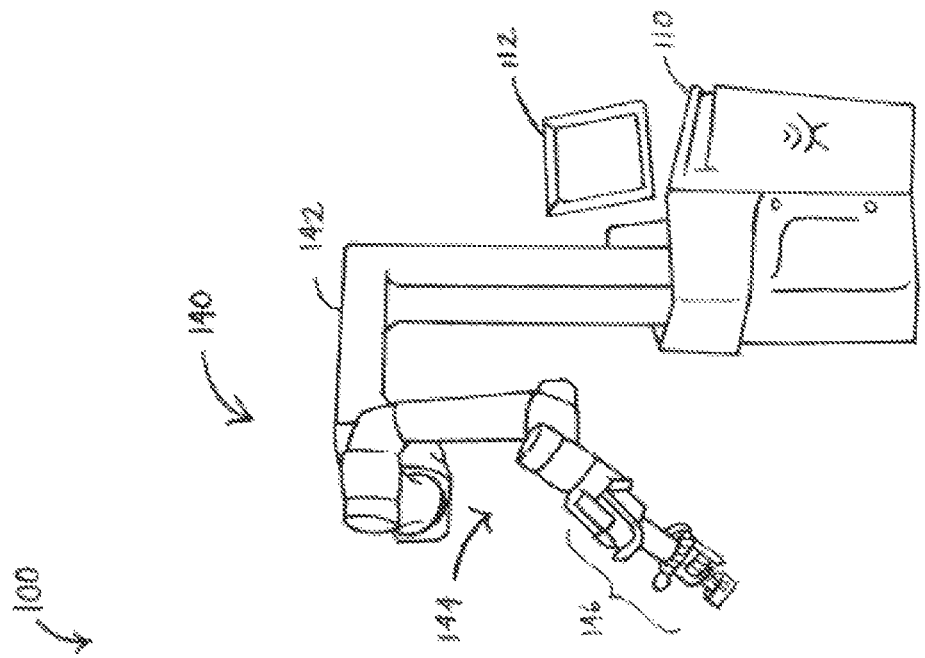
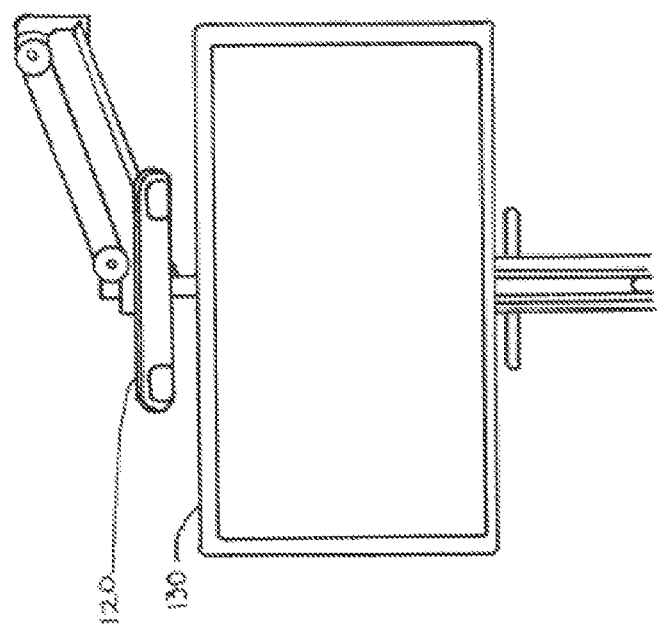
FIG. 1

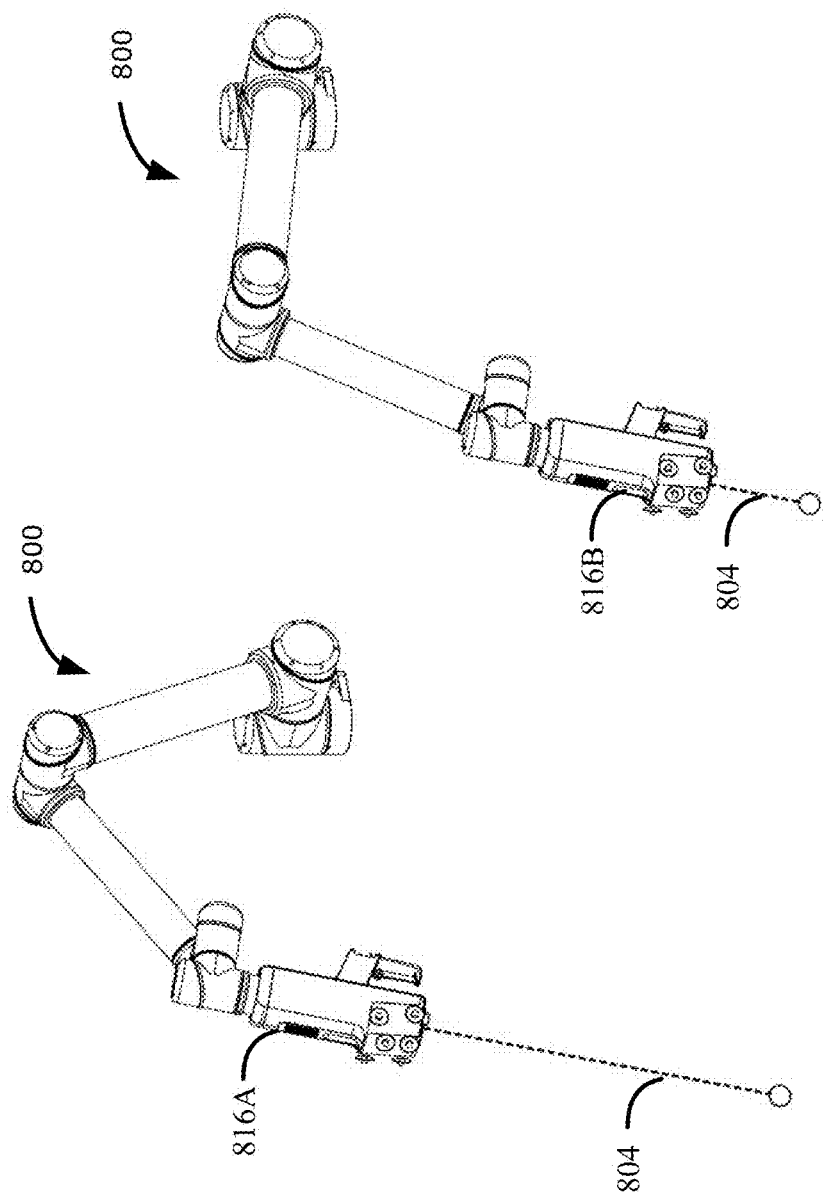

POSITIONING ARM FOR A SURGICAL NAVIGATION SYSTEM

REFERENCE TO PRIOR APPLICATIONS

This application is a continuation of U.S. application Ser. No. 16/114,323, filed on Aug. 28, 2018, which claims priority from Canadian Application No. 2,977,489, filed Aug. 28, 2017, the entireties of which are incorporated herein by reference.

FIELD

The present application generally relates to a surgical navigation system and, in particular, to a positioning arm for the surgical navigation system.

BACKGROUND

Surgical navigation systems may include frames and structures for positioning and manipulating surgical instruments, such as microscopes, cutting instruments, probes, light sources, etc. In some scenarios, precise placement of surgical instruments may be crucial to successfully conducting a surgical procedure. Frames and structures of common surgical navigation systems may facilitate positioning and re-positioning medical instruments throughout a surgical procedure. However, positioning and re-positioning of medical instruments using such existing frames and structures requires manual and intricate user input.

BRIEF SUMMARY

In one aspect, the present application describes a motion-assisted positioning arm for a medical procedure. The positioning arm includes a base; an arm including: a plurality of arm segments extending from a first arm end to a second arm end, the arm being coupled to the base at the first arm end; and a plurality of joints for connecting arm segments, wherein each arm segment in the plurality of arm segments is connected to an adjacent arm segment by a joint in the plurality of joints; an end effector coupled to the second arm end such that the end effector is manipulable with six degrees of freedom in a task-coordinate space based on motion by at least one joint in the plurality of joints; a processor coupled to the plurality of joints and the end effector; and a memory coupled to the processor and storing processor-readable instructions. The processor-readable instructions may cause the processor to: detect manipulation of the end effector and determine forces or torques acting on the end effector; determine a surgical mode for constraining movement of the end effector in the task-coordinate space; determine an end effector velocity based on the determined forces or torques and the surgical mode for moving the end effector in the task-coordinate space; and apply at least one joint space movement in the plurality of joints based on the end effector velocity.

In another aspect, the present application describes processor-readable instructions that, when executed, configure a processor to perform one or more of the operations described herein. In this respect, the term processor is intended to include all types of processing circuits or chips capable of executing program instructions.

Other aspects and features of the present application will be understood by those of ordinary skill in the art from a review of the following description of examples in conjunction with the accompanying figures.

BRIEF DESCRIPTION OF THE DRAWINGS

Reference will now be made, by way of example, to the accompanying drawings which show example embodiments of the present application.

FIG. 1 features components of a surgical navigation system, in accordance with an embodiment of the present application;

FIGS. 8A and 8B illustrate configurations of the positioning arm while in the stand-off mode, in accordance with an embodiment of the present application;

Similar reference numerals may have been used in different figures to denote similar components.

DESCRIPTION OF EXAMPLE EMBODIMENTS

Figure 2:
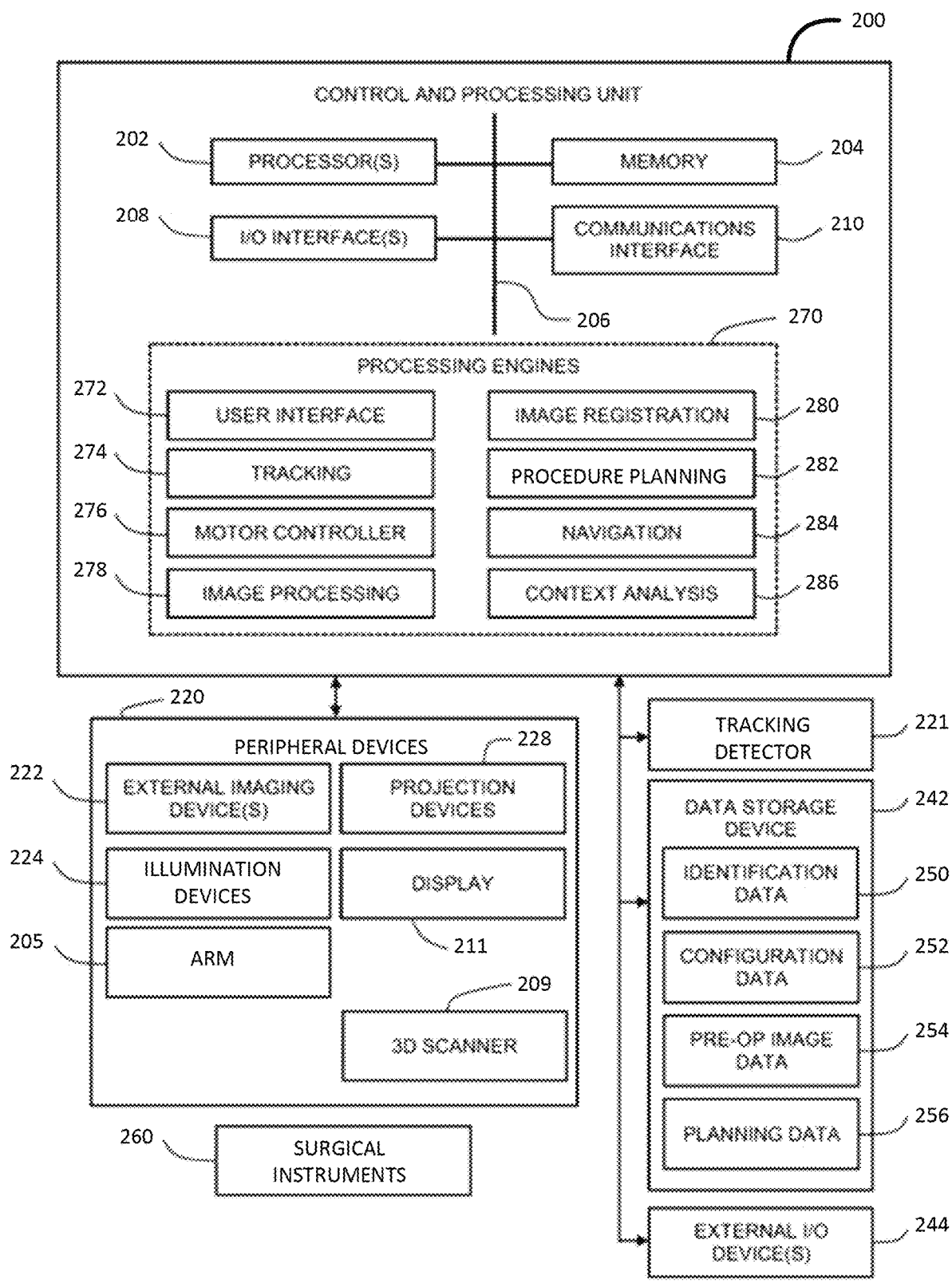
FIG. 2 illustrates a block diagram of the surgical navigation system of FIG. 1, in accordance with an embodiment of the present application.

Various examples and aspects of the present application will be described with reference to the details discussed below. The following description and drawings are illustrative of the present application and are not to be construed as limiting the present application. Numerous details are described to provide a thorough understanding of various embodiments. However, in certain instances, well-known or conventional details are not described in order to provide a concise discussion of the embodiments of the present application.

As used herein, the terms "comprises" and "comprising" are to be construed as being inclusive and open ended, and not exclusive. Specifically, when used in the specification and claims, the terms "comprises" and "comprising" and variations thereof mean the specified features, steps, or components are included. These terms are not to be interpreted to exclude the presence of other features, steps, or components.

As used herein, the term "exemplary" means "serving as an example, instance, or illustration", and should not be construed as preferred or advantageous over other configurations disclosed herein.

As used herein, the terms "about", "approximately", and "substantially" are meant to cover variations that may exist in the upper and lower limits of the ranges of values, such as variations in properties, parameters, and dimensions. In a non-limiting example, the terms "about", "approximately", and "substantially" may mean plus or minus 10 percent or less.

As used herein, the phrase "intraoperative" refers to an action, process, method, event or step that occurs or is carried out during at least a portion of a medical procedure. Intraoperative, as defined herein, is not limited to surgical procedures, and may refer to other types of medical procedures.

In the present application, the term "and/or" is intended to cover all possible combination and sub-combinations of the listed elements, including any one of the listed elements alone, any sub-combination, or all of the elements, and without necessarily excluding additional elements.

In the present application, the phrase "at least one of . . . or . . . " is intended to cover any one or more of the listed elements, including any one of the listed elements alone, any sub-combination, or all of the elements, without necessarily excluding any additional elements, and without necessarily requiring all of the elements.

Medical professional have traditionally relied upon what they see and have relied upon their own hands for positioning or manipulating medical instruments, such as microscopes, cutting instruments, probes, light sources, etc. With advances in technology, surgical navigation systems are increasingly used by medical professionals for providing intraoperative imaging functionality for assisting with conducting medical procedures. For example, surgical navigation systems may include arms for positioning imaging devices adjacent to surgical points of interest or surgical orifices. The images captured by these imaging devices may be projected onto displays, such that the surgical point of interest may be more easily examined.

Because surgical points of interests or surgical orifices are commonly located near or within confined spaces, positioning of surgical instruments, such as imaging devices, that are affixed to positioning arms may require intricate effort, such that the surgical instruments do not make contact with or accidentally damage tissue adjacent the surgical point of interest. Thus, manipulating and positioning surgical instruments that are affixed to positioning arms may require intricate effort. It may be desirable to provide a motion-assisted positioning arm that may apply constraints to the movement of surgical instruments affixed to positioning arms. Although the example above describes affixing imaging devices to the positioning arm, other surgical instruments, such as probes or cutting instruments, may also be held by and manipulated by positioning arms during surgical procedures.

Some surgical navigation systems may include imaging devices having fixed focal length lenses. In such surgical navigation system configurations, it may be desirable to maintain a focal distance between the imaging device lens and the surgical point of interest. However, if the medical professional would like a view of the surgical point of interest from a different perspective or view point, it may be cumbersome and time consuming to re-position the positioning arm such that: (1) the imaging device may capture the surgical point of interest from the different view point; while (2) the imaging device may be positioned to maintain the previous focal distance between the imaging device lens and the surgical point of interest. According, it may be desirable to constrain movement of surgical instruments, such as the imaging device described above, to particular movement paths for re-positioning or manipulating surgical instruments.

Reference is now made to FIG. 1, which illustrates components of a surgical navigation system 100, in accordance with an embodiment of the present application. The surgical navigation system 100 may include an equipment tower 110, a tracking detector 120, a display 130, and a positioning arm 140. In some examples, the equipment tower 110 may be positioned adjacent the positioning arm 140, as illustrated in FIG. 1. As will be described herein, the equipment tower 110 may include a control and processing unit for the surgical navigation system. In some examples, the equipment tower 110 may include an equipment tower display 112 for receiving input from a medical professional or providing output to the medical professional relating to the operation of the surgical navigation system 100.

The tracking detector 120 may include an optical tracking device, such as a tracking camera, a video camera, a three-dimensional scanner, or any other suitable imaging device for detecting fiducial markers or landmark features within an operating room environment. The display 130 may be configured to display images of a surgical site/point of interest to the medical professional, such that the surgical site/point of interest may be enlarged for easier viewing. The tracking detector 120 and the display 130 may be in communication with the equipment tower 110.

The positioning arm 140 may include a base 142 and an arm 144. The arm 144 may include a plurality of arm segments extending from a first arm end to a second arm. The arm 144 may be coupled to the base 142 at the first arm end. The arm 144 may also include a plurality of joints for connecting arm segments. Each arm segment in the plurality of arm segments may be connected to an adjacent arm segment by a joint in the plurality of joints.

The positioning arm 140 may include an end effector 146 coupled to the second arm end. The end effector 146 may be manipulable with six degrees of freedom in a task-coordinate space based on motion by at least one joint in the plurality of joints. In some embodiments, the task-coordinate space may be a three-dimensional Cartesian coordinate space for tracking movement and position of the end effector in an operating room environment. For example, an origin position (0,0,0) may be a pre-defined position in the task-coordinate space, and movement and positions of the end effector may be relative to the origin position. Movement of the end effector 146 in the example task-coordinate space may include movement in at least one of the x-axis direction, the y-axis direction, or the z-axis direction and may include rotation about at least one of the x-axis direction, the y-axis direction, or the z-axis direction in the task-coordinate space. A three-dimensional Cartesian coordinate space is provided as an example; however, other types of coordinate spaces may be implemented for the task-coordinate space.

The end effector 146 may include a force-moment sensor for determining forces and torques acting on the end effector 146. That is, if the medical professional were to push the end effector 146 to urge the end effector 146 towards or away from the origin position, the force-moment sensor may detect that the end effector 146 is being manipulated and may determine forces and torques acting on the end effector 146. In some embodiments, the forces and torques imparted on the end effector 146 may be determined in relation to an effector-coordinate space. The effector-coordinate space may be associated with the end effector 146 while the end effector 146 may be tracked and may move through different positions in the task-coordinate space. That is, the effector-coordinate space may be a coordinate space for tracking forces and/or torques acting on the end effector 146. In some examples, the effector-coordinate space may be a Cartesian coordinate space; however, some other embodiments, other coordinate spaces may be used.

For example, the determined forces and torques imparted on the end effector 146 may include a translational force having a magnitude and direction in at least one of an x-axis, y-axis, or z-axis direction of the effector-coordinate space. The determined torques may include a torque for rotating the end effector in at least one of a pitch, yaw, or roll orientation of the effector-coordinate space.

In some embodiments, the end effector 146 may include one or more fiducial markers affixed thereto, and the surgical navigation system 100 may track, using the tracking detector 120, the position or movement of the end effector 146 in the task-coordinate space.

For example, if the task-coordinate space is the three-dimensional Cartesian coordinate space, the surgical navigation system 100 may be configured to identify the position of the end effector 146 according to x, y, and z coordinates and the orientation of the end effector 146 in the task coordinate space. In some other embodiments, the surgical navigation system 100 may track the position and orientation of the end effector 146 using various image recognition methods.

The end effector 146 may be configured to receive surgical instruments, such as imaging devices or surgical tools. That is, the positioning arm 140 may be configured to position imaging devices or surgical tools at prescribed positions and orientations within the task-coordinate space. For example, imaging devices may include microscopes or digital still cameras, and the imaging devices may be positioned by the end effector 146 adjacent a surgical site or a point of interest such that an image may be displayed on the display 130 for viewing by the medical professional and support staff. Other imaging devices may also be affixed to the end effector 146, including wide field cameras, microscope and Optical Coherence Tomography (OCT) devices, video cameras, three-dimensional scanners, or other imaging instruments. Surgical tools may include probes or cutting tools that may be held in a static position during portions of a surgical procedure, and that may be adjusted at various times during the surgical procedure.

The surgical navigation system 100 may include a greater or fewer number of components than that illustrated in FIG. 1. For example, the surgical navigation system may include two or more positioning arms having different imaging devices or instruments coupled thereto. Although the end effector 146 may be described as being coupled to the second arm end, in some embodiments, the end effector 146 may be integrated into the arm segment at the second arm end. That is, the end effector 146 need not be a discrete feature that is independent of arm segments.

Reference is now made to FIG. 2, which illustrates a block diagram of components of an example components of the surgical navigation system 100 of FIG. 1, in accordance with an embodiment of the present application. The surgical navigation system 100 may include a control and processing unit 200. In some examples, the control and processing unit 200 may be included within the equipment tower 110 (FIG. 1). The control and processing unit 200 may include one or more processors 202, memory 204, a system bus 206, input/output interfaces 208, and a communication interface 210.

The control and processing unit 200 may interface with external devices, including a tracking detector 221, which in some examples may be the tracking detector 120 of FIG. 1. The control and processing unit 200 may also interface with a data storage device 242. The data storage device 242 may include local or remote memory devices, such as hard drives, digital media devices, or server devices, having storage and/or database capabilities therein. As illustrated in FIG. 2, the data storage device 242 may include identification data 250, such as data for identifying surgical instruments 260. The data storage device 242 may also include configuration data 252 for the surgical navigation system 100. The data storage device 242 may also include pre-operative image data 254 and medical procedure planning data 256. Pre-operative image data 254 may include previously acquired patient or preoperative images. Although the data storage device 242 is illustrated as a collective device in FIG. 2, in some examples, the plurality of data types illustrated in FIG. 2 may be provided across multiple data storage devices.

The control and processing unit 200 may also interface with external input/output devices 244. To illustrate, the control and processing unit 200 may interface with peripheral devices 220. Example peripheral devices 220 include external imaging devices 222, illumination devices 224, one or more arms 205 (which in some examples may be the positioning arm 140 of FIG. 1), projection devices 228, three-dimensional scanner 209, or a display 211 (which in some examples may be the display 130 of FIG. 1). In some examples, the three-dimensional scanner 209 may include preoperative or intraoperative imaging devices, such as computerized tomography (CT), magnetic resonance imaging (MRI), ultrasound, ocular coherence tomograph (OCT), or structured light imaging probe devices. In some examples, external imaging devices 222 or three-dimensional scanner 209 may have a physical form-factor that may be mounted to the end effector 146 (FIG. 1) and positioned or manipulated in the task-coordinate space by the arm 205.

In some embodiments, the control and processing unit 200 may be configured to track the position and orientation of the end effector 146 (FIG. 1) or surgical instruments 260 based on input from peripheral devices 220 and other external devices. For example, the tracking detector 221 may be configured to detect and acquire data relating to the end effector 146 having one or more fiducial markers affixed thereto. The control and processing unit 200 may be configured to register the detected end effector 146 to reference frames in the task-coordinate space. That is, when the tracking detector 221 detects the one or more fiducial marker affixed to the end effector 146, the control and processing unit 200 may register the position and orientation of the detected end effector 146 to the task-coordinate space. In some examples, identification data 250 associated with the one or more fiducial markers attached to the end effector 146 may be used for identifying the surgical instruments 260 in the task-coordinate space.

Example methods described in the present application include operations that may be implemented, at least in part, through processor-executable instructions stored, for example, in the memory 204 or stored in the data storage device 242, described above. In some examples, the control and processing unit 200 may include processing engines 270. The processing engines 270 may be dedicated processing resources for specified tasks. For example, the processing engines 270 may include a user interface engine 272, a tracking engine 274, a motor controller engine 276, an image processing engine 278, an image registration engine 280, a procedure planning engine 282, a navigation engine 284, and a context analysis engine 286. The processing engines 270 may be illustrated as separate processing engines. However, in some examples, the processor 202 may dynamically allocate processing engine resources.

Figure 3:
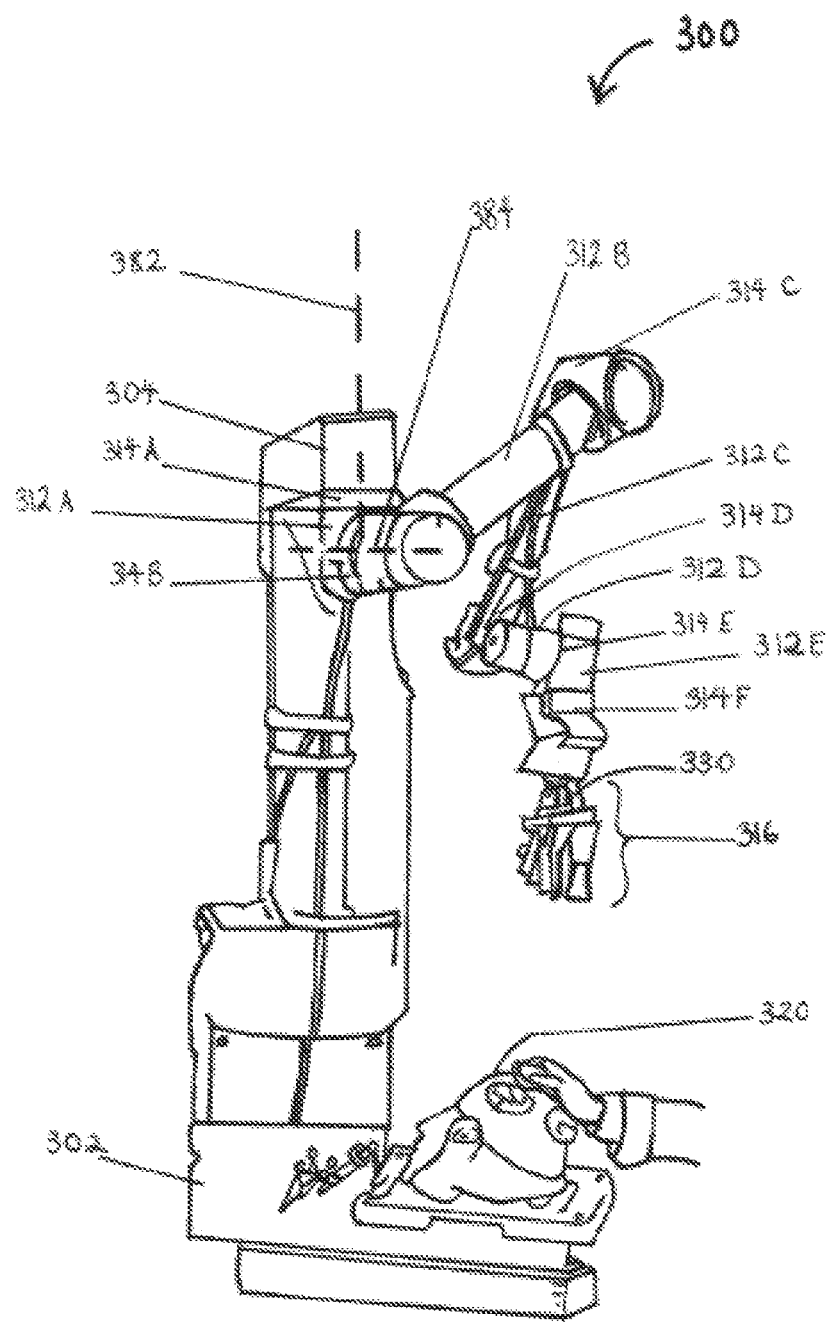
FIG. 3 illustrates a perspective view of a positioning arm for a surgical navigation system, in accordance with an embodiment of the present application.

Reference is now made to FIG. 3, which is a perspective view of a positioning arm 300 for the surgical navigation system 100 of FIG. 1, in accordance with an embodiment of the present application. The positioning arm may be a motion-assisted positioning arm for a medical procedure. In some embodiments, the medical procedure may include any one of surgical navigation, robotic surgery, robotically-assisted surgery, an ophthalmology procedure, or an endoscopy procedure. Although the above describes a list of example procedures, the motion-assisted positioning arm may be for any other type of medical procedure.

As illustrated in FIG. 3, the positioning arm 300 may be adjacent a surgical procedure bench 302, and the surgical procedure bench 302 may be for positioning a patient for a duration of the medical procedure. For example, the surgical procedure bench 302 may be an operating room table and a patient may be positioned on the operating room table for the duration of the medical procedure. In FIG. 3, the patient or a surgical site is illustrated as a training device 320 representing an example patient on which a medical procedure is to be performed. In some examples, the surgical site may be a point of interest that may be used as a reference point for one or more surgical modes of the positioning arm 300. Surgical modes of the positioning arm 300 will be described herein.

The positioning arm 300 may include a base 304. To illustrate, the base 304 may include a vertical column and a horizontal support that is perpendicular to and that is coupled to the vertical column. In some examples, the base 304 may be any other shape or configuration suitable for supporting an arm as described herein.

The positioning arm 300 may include an arm, where the arm includes a plurality of arm segments. In the example illustrated in FIG. 3, the plurality of arm segments includes a first arm segment 312a, a second arm segment 312b, a third arm segment 312c, a fourth arm segment 312d, and a fifth arm segment 312e. Although five arm segments are described with reference to FIG. 3, in other examples, the positioning arm 300 may include fewer or more arm segments. The plurality of arm segments may extend from a first arm end to a second arm end. The arm may be coupled to the base 304 at the first arm end. In particular, in FIG. 3, the plurality of arm segments extends from the first arm segment 312a to the fifth arm segment 312e. The first arm segment 312a may be at the first arm end. The fifth arm segment 312e may be at the second arm end.

The arm may include a plurality of joints for connecting the plurality of arm segments. The plurality of joints may include a first joint 314a, a second joint 314b, a third joint 314c, a fourth joint 314d, a fifth joint 314e, and a sixth joint 314f. Although six joints are described with reference to FIG. 3, in other examples, the positioning arm 300 may include fewer or more joints. Each arm segment in the plurality of arm segments may be connected to an adjacent arm segment by a joint in the plurality of joints. For example, the second joint 314b may connect the first arm segment 312a with the second arm segment 312b.

The arm may also include an end effector 316 which may be configured to receive an imaging device 330 or surgical tools. An example imaging device 330 may include microscopes, digital video cameras, projection devices, three-dimensional scanners, etc. Surgical tools may include cutting tools, probe tools, etc. In the example illustrated in FIG. 3, the first joint 314a may couple the first arm segment 312a to the base 304, and the sixth joint 314f may couple the fifth arm segment 312e to the end effector 316.

In some embodiments, the end effector 316 may include a force-moment sensor for determining forces and torques acting on the end effector 316. The force-moment sensor may be coupled to the one or more processors 202 (FIG. 2), such that the surgical navigation system 100 (FIG. 1) may implement operations for detecting manipulation of the end effector 316 and determining forces and torques acting on the end effector 316. For example, the determined force may include a determined magnitude and direction associated with movement in an x-axis, y-axis, or z-axis of a three-dimensional Cartesian coordinate space. The determined torque may include a determined magnitude and direction associated with rotations about the x-axis, y-axis, or z-axis directions in the task-coordinate space.

The end effector 316 may also include a handle for receiving input from the medical professional. The medical professional may desire that the imaging device 330 affixed to the end effector 316 be re-positioned to capture images of the surgical site from a different viewpoint or perspective. Accordingly, the medical professional may grasp the end effector handle and attempt to move the end effector 316 to another position or orientation in the task-coordinate space. The surgical navigation system 100 may detect that the end effector 316 is being manipulated, and may determine the forces or torques acting on the end effector 316. As will be described herein, the surgical navigation system 100 may determine an end effector velocity based on the determined forces and torques and a surgical mode for defining a new end effector position in the task-coordinate space.

In some embodiments, the end effector 316 may include an engagement switch (not explicitly illustrated in FIG. 3) for enabling detection of end effector manipulation. For example, the engagement switch may be a touch sensor, and the end effector 316 may be configured to enable detection of movement in the end effector when the touch sensor detects the presence of the user. In another example, the engagement switch may be an engagement button, and the end effector 316 may be configured to enable detection of movement in the end effector when the engagement button is depressed. That is, the engagement button may be depressed when the medical professional grasps an end effector handle. The end effector engagement switch may be useful for ensuring that the positioning arm detects intentional manipulation of the end effector 316, rather than accidental contact with the end effector. For example, when a medical professional accidentally bumps into the end effector, the positioning arm 300 may be configured to disregard the accidental input unless the engagement switch is engaged.

As described, the arm may include a plurality of joints for connecting arm segments. Each joint may be may include at least one of a revolute joint, a prismatic joint, or a flexible joint. For example, a revolute joint may be a joint rotating or revolving about a reference axis. A prismatic joint may impart movement between two segments or bodies in a linear direction. A flexible joint may couple two segments or bodies which may not be aligned. For example, flexible joints may include joints utilized with soft robotics.

To illustrate, in FIG. 3, the first joint 314a may be a revolving joint, and the first arm segment 312a may be coupled to the base 304 via the first joint 314a such that the first arm segment 312a may rotate about a first axis 382, as illustrated in FIG. 3. In another example, the second joint 314b may be a revolute joint, allowing the first arm segment 312a to exhibit rotating or revolving motion about a rotary axis 384 relative to the second arm segment 312b. In FIG. 3, the first axis 382 associated with the first joint 314a may be perpendicular to the rotary axis 384 associated with the second joint 314b.

The plurality of joints illustrated in FIG. 3 are meant to be examples of joints that may be used for the positioning arm 300; however, it will be appreciated that each of the plurality of joints may be selected and configured such that an end effector 316 coupled to the second arm end may be manipulable with six degrees of freedom in the task-coordinate space based on motion by at least one joint in the plurality of joints.

Each joint in the plurality of joints may also include an actuator (not explicitly illustrated) for facilitating movement among adjacent arm segments connected by the respective joint in the plurality of joints. That is, each actuator may independently facilitate movement among adjacent arm segments connected by the joint of that respective actuator.

For example, the second joint 314b may include an actuator for causing rotational movement as between the first arm segment 312a and the second arm segment 312b about the rotary axis 384. Because each joint in the plurality of joints includes an actuator for facilitating movement among adjacent arm segments connected by the respective joint, the positioning arm 300 may be a motion-assisted positioning arm, whereby forces and torques imparted on the end effector 316 may result in actuator-assisted movement of the end effector 316 according to the detected forces and torques imparted on the end effector 316.

Each joint in the plurality of joints may also include a joint encoder for determining a joint position. For example, because the second joint 314b may be a revolute joint, the joint encoder for the second joint 314b may be configured to determine an angular position about the rotary axis 384 of the first arm segment 312a relative to the second arm segment 312b. In another example, for the sixth joint 314f, the joint encoder for the sixth joint 314f may be configured to determine an angular position of the end effector 316 relative to a "0 degree" reference point on the fifth arm segment 312e.

The joint encoders may be coupled to the one or more processors 202 such that the surgical navigation system 100 (FIG. 1) may implement operations, in response to joint position information from joint encoders, for determining at least one joint space movement in the plurality of joints for positioning the end effector 316 at an updated position in the task-coordinate space. Accordingly, in some embodiments, the surgical navigation system 100 may periodically receive data or information relating to forces and torques acting on the end effector 316 and may periodically receive other positioning arm parameters, including joint angular position from the respective joint encoders, for implementing operations described herein.

Accordingly, the surgical navigation system 100 may include one or more processors 202 coupled to (1) the plurality of joints, where each joint in the plurality of joints may include an actuator for facilitating movement and a joint encoder; and (2) the end effector 316, where the end effector 316 may include a force-moment sensor for detecting manipulation of the end effector and for determining forces and torques acting on the end effector 316. Based on the detected forces and torques acting on the end effector 316, the positioning arm 300 may determine an end effector velocity based on determined forces and torques acting on the end effector for defining an updated end effector position in the task-coordinate space. In some embodiments, the surgical navigation system 100 may determine or track the detected forces and torques acting on the end effector 316 with reference to the effector-coordinate space. As described, the effector-coordinate space may be associated with the end effector 316 and may move within the task-coordinate space as the end effector 316 moves through the task-coordinate space.

Further, the positioning arm 300 may determine at least one joint space movement in the plurality of joints using inverse arm kinematics for positioning the end effector at the new position in the task-coordinate space. Inverse arm kinematics may be kinematic equations to determine joint parameters for facilitating movement in at least one joint of the plurality of joints. The one or more processors 202 may transmit the determined joint parameters to the actuator in the respective joints for facilitating movement in the respective joints, such that the end effector 316 may be transitioned to the updated position in the task-coordinate space. Because the actuators may impart movement among arm segments, any movement of the arm segments may be motion-assisted by the actuators.

Figure 4:
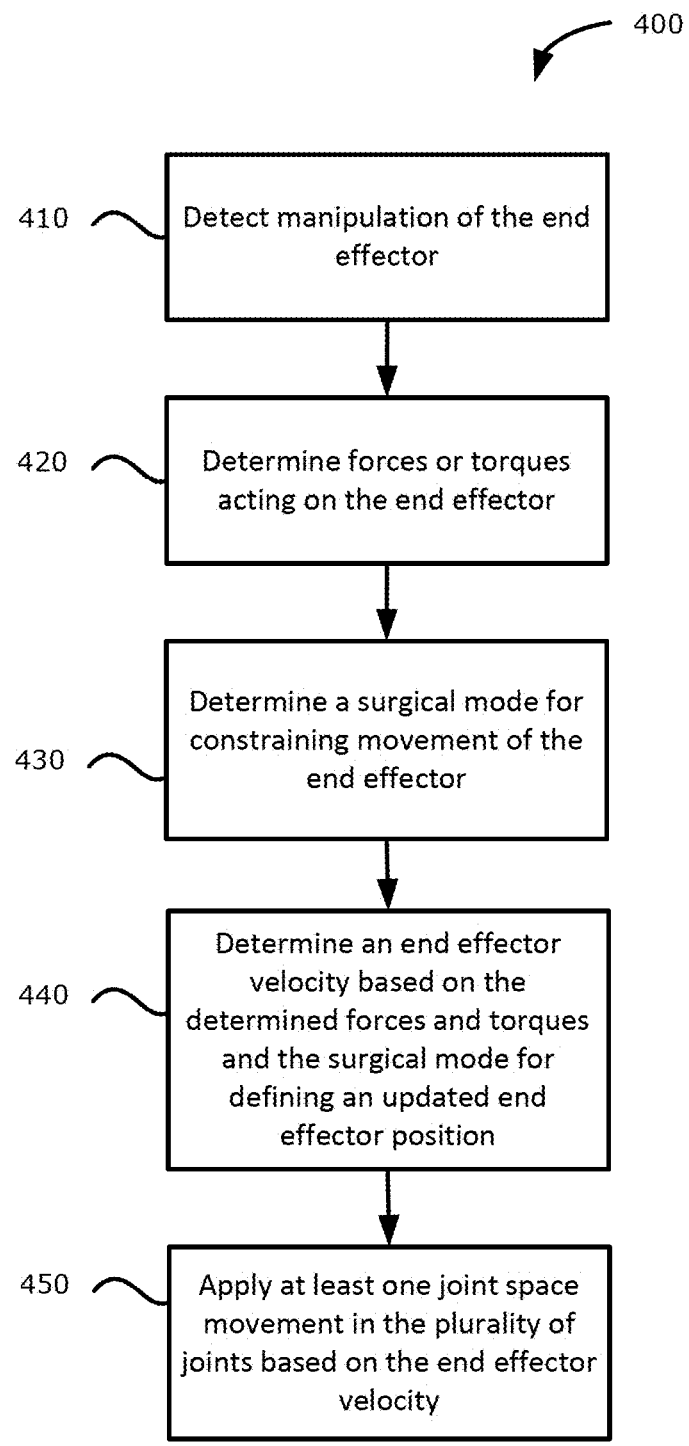
FIG. 4 illustrates, in flowchart form, a method of positioning an end effector, in accordance with an embodiment of the present application.

Reference is now made to FIG. 4, which illustrates, in flowchart form, a method 400 of positioning the end effector 316 of FIG. 3, in accordance with an embodiment of the present application. The method 400 may include operations that may be carried out generally by the surgical navigation system 100 (FIG. 1) or by the positioning arm 300 (FIG. 3). The method 400 may be implemented, at least in part, through processor-executable instructions stored for example at the data storage device 242 (FIG. 2). For example, the processor-executable instructions may be executed by a processor 202 (FIG. 2). In some examples, one or more of the operations may be implemented via processor-executable instructions stored in the memory 204 (FIG. 2) or other data storage devices. For ease of exposition in the description that follows, the task-coordinate space may be a three-dimensional Cartesian coordinate space. However, embodiments of the present application may incorporate any other types of coordinate space for the task-coordinate space.

At operation 410, the processor 202 may detect manipulation of the end effector 316. The processor 202 may determine that the end effector 316 has been manipulated if the position of the end effector 316 has been shifted in any of the x-axis, y-axis, or z-axis directions. Further, the processor 202 may determine that the end effector 316 has been manipulated if the orientation of the end effector 316 has been altered in any of the pitch, yaw, or roll orientations.

For example, if a medical professional grasps the end effector 316 and displaces the end effector 316 from a current end effector position in the task-coordinate space, at operation 420, the processor 202 may determine forces or torques acting on the end effector 316. For example, when the end effector 316 is displaced from its current position, the processor 202 may determine a force acting on the end effector 316 for displacing the end effector 316 to an updated end effector position in the task-coordinate space. The force may include a magnitude and a direction. In addition, when the end effector 316 is displaced from its current orientation, the processor 202 may determine a torque for displacing the end effector 316 to an updated orientation in the task-coordinate space.

To illustrate, the positioning arm 300 may be initialized with the end effector 316 at an origin position in the task-coordinate space of an operating room environment. For example, the origin position may be a predefined position in the task-coordinate space. Upon detection of manipulation of the end effector 316, the processor 202 may determine a force or torque acting on the end effector 316. The force may include a magnitude and a direction associated with displacing the end effector 316 or moving the end effector 316 in a specified direction in the task-coordinate space. As an illustrating example, the force may cause the end effector 316 to be displaced to a location that may be 3 units along an x-axis, 2 units along a y-axis, and 5 units along a z-axis of the task-coordinate space. Accordingly, the force may cause the end effector 316 to move to a position defined by the coordinates (3, 2, 5) in the task-coordinate space. Further, the force may cause the end effector 316 to be oriented in an updated end effector orientation. For example, the torque may cause the end effector 316 to be rotationally displaced in at least one of the pitch, yaw, or roll directions. Accordingly, at operation 420, the processor 202 may determine forces or torques acting on the end effector 316. As described, the determined forces or torques may be utilized for determining movement of the end effector 316 in the task-coordinate space, and the result of the movement may result in the end effector 316 moving to a new position in the task-coordinate space.

At operation 430, the processor 202 may determine a surgical mode for constraining movement of the end effector in the task-coordinate space. In some embodiments, the processor 202 may determine the surgical mode based on input from an input interface. For example, the equipment tower display 112 (FIG. 1) may be a touch-screen display. The medical professional may provide, via the touch-screen display, a desirable surgical mode for constraining movement of the end effector in the task-coordinate space. In some other examples, the medical professional may provide the desirable surgical mode via other input devices, such as pointing devices, trackpad devices, keyboard devices, voice command input, etc.

In some embodiments, the surgical modes may include a free motion mode, a roll mode, a translate mode, a stand-off mode, and an orbit mode. In some examples, the free motion mode may allow the end effector 316 to move freely in all directions and in all orientations. That is, an updated end effector position in a task-coordinate space is based on a totality of forces and torques detected at the end effector 316. The roll mode may fix the end effector position in the task-coordinate space, while allowing orientation changes about a roll axis of the end effector 316. The translate mode may fix the orientation of the end effector 316 within the task-coordinate space, while allowing positional changes in the task-coordinate space. For example, the processor 202 may allow movement along the x-axis, y-axis, or z-axis directions, while maintaining the pitch, yaw, or roll orientation of the end effector 316. The stand-off mode may fix the orientation of the end effector 316 within the task-coordinate space, while allowing the end effector 316 to move towards or away from a previously defined point of interest along a stand-off axis. The orbit mode may fix the end effector position or orientation such that the end effector 316 may move about a previously defined point of interest at a fixed distance. Accordingly, the orbit mode may allow an end effector 316 to move in an orbit along a surface of a notional spherical volume. Further description of the example surgical modes will follow in the description herein.

At operation 440, the processor 202 may determine an end effector velocity based on (1) the determined forces and torques; and (2) the surgical mode for defining an updated end effector position in the task-coordinate space. The end effector velocity may include a magnitude and direction. In some examples, the end effector velocity may be based on a combination of the force and the torque acting on the end effector 316.

In some embodiments, to determine the end effector velocity, the processor 202 may determine, based on the surgical mode, a subset of the forces and torques acting on the end effector to use for determining the end effector velocity. Further, to determine the end effector velocity, the processor 202 may discard, based on the surgical mode, remaining forces and torques acting on the end effector when determining the end effector velocity.

To illustrate operation 440, reference is now made to FIGS. 5A, 5B, 5C, and 5D, which illustrate example surgical modes for constraining movement of the end effector 316 (FIG. 3) in the task-coordinate space.

Figure 5A:
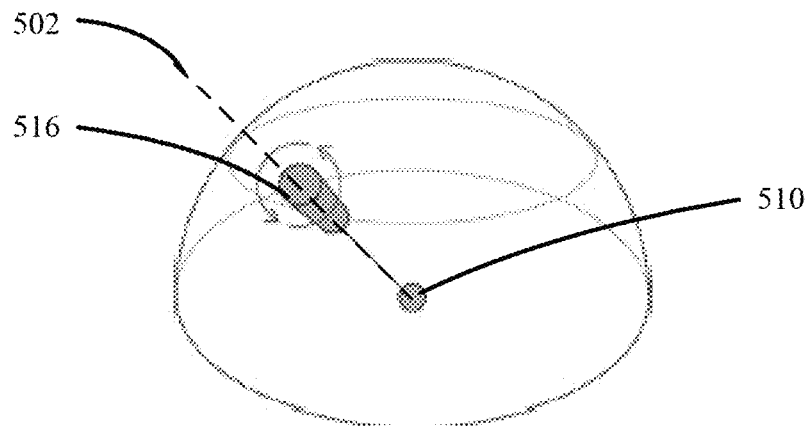
FIGS. 5A, 5B, 5C, and 5D illustrate example surgical modes for constraining movement of an end effector that is coupled to the positioning arm of FIG. 3, in accordance with an embodiment of the present application.

In particular, FIG. 5A illustrates the roll mode described herein. The roll mode may fix the end effector position in the task-coordinate space, while allowing orientation changes about a roll axis of the end effector 316 based on determined forces and torques acting on the end effector 316. In the roll mode, the processor 202 may determine a roll axis 502 for an end effector 516. For example, the end effector 516 illustrated in FIG. 5A may correspond to the end effector 316 of the positioning arm 300 of FIG. 3. As illustrated in FIG. 5A, the roll axis 502 for the end effector 516 may intersect a surgical point of interest 510.

In the roll mode, the processor 202 may subsequently determine a roll torque about the roll axis 502 from the determined forces and torques acting on the end effector 516. For example, the processor 202 may determine that the torque acting on the end effector 516 may displace or adjust the orientation of the end effector 516 in a roll orientation in the task-coordinate space.

Accordingly, the processor 202 may be configured to determine, at operation 440, an end effector velocity based on the roll torque acting on the end effector 516, while discarding all other forces and torques of the determined forces and torques acting on the end effector 516. That is, the processor 202 may determine a torque for adjusting the roll orientation of the end effector 516 about the roll axis 502, and may subsequently determine the end effector velocity based on the torque, while discarding forces and torques that may displace the end effector 516 in any other orientation or direction. For example, the processor may discard any forces that may cause the end effector 516 to move towards or away from the surgical point of interest 510.

In some embodiments, if the end effector 516 is configured to affix an imaging camera thereto, in the roll mode, the end effector 516 may maintain a distance between the imaging camera and the surgical point of interest 510, while allowing rotation of the imaging camera for altering the view of captured images. Fixing the end effector 516 in a position in the task-coordinate space prevents inadvertent movement of the end effector 516 within confined surgical orifices, thereby preventing inadvertent injury or damage to surrounding tissues.

Figure 5B:
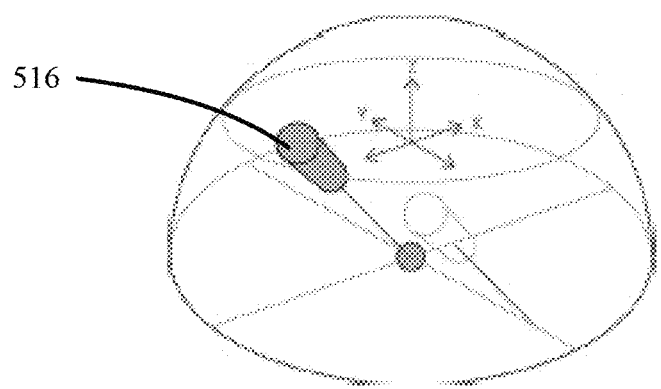

FIG. 5B illustrates the translate mode described herein. The translate mode may maintain orientation of the end effector 516, while allowing position changes about one or more axis of the task-coordinate space. For example, in contrast to the roll mode illustrated in FIG. 5A, the translate mode may maintain the orientation of the end effector 516, thereby disallowing pitch, yaw, or roll movements in the task-coordinate space. The translate mode, however, may allow positional movement in one of or a combination of the x-axis, y-axis, or z-axis directions of the task-coordinate space.

Accordingly, at operation 440, the processor 202 may be configured to determine the end effector velocity based on a totality of forces acting on the end effector, while discarding torques acting on the end effector. The end effector velocity associated with the end effector 516 may transition the end effector 516 in at least one of x-axis, y-axis, or z-axis directions while eliminating pitch, yaw, and roll movement in the end effector 516. Fixing the orientation of the end effector 516 may be useful when the medical professional may desire to view different points in a surgical space while maintaining the orientation of an imaging device affixed to the end effector 516. For example, the translate mode may be useful for creating a "wide-angle" or panoramic-type view of a surgical point of interest.

Figure 5C:
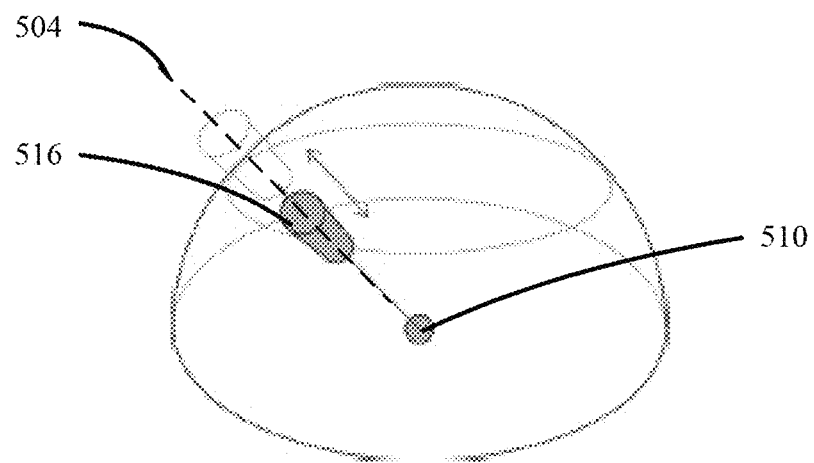

FIG. 5C illustrates the stand-off mode described herein. The stand-off mode may maintain orientation of the end effector 516, while allowing position changes along a stand-off axis of the end effector 516. In the stand-off mode, the processor 202 may determine a stand-off axis for the end effector 516. As illustrated in FIG. 5C, the stand-off axis 504 for the end effector 516 may be an axis adjoining, for example, the surgical point of interest 510 and the end tip of the end effector 516. That is, the stand-off axis may intersect with the surgical point of interest 510.

Accordingly, in the stand-off mode, the processor 202 may be configured to determine, at operation 440, an end effector velocity based on forces acting on the end effector along the stand-off axis 504, while discarding all other forces not acting along the stand-off axis 504 and discarding torques acting on the end effector 516. That is, the processor 202 may be configured to determine an end effector velocity based on a force acting on the end effector causing a movement in the end effector 516 in the stand-off axis 504 direction. Further, the processor 202 may be configured to discard or ignore the torque acting on the end effector. Overall, the stand-off mode may fix the orientation of the end effector 516 such that an imaging camera affixed to the end effector 516 will continue to capture images of the surgical point of interest 510, while altering the distance between the imaging camera lens and the surgical point of interest 510. Fixing end effector movements to the stand-off axis 504 may be useful when the medical professional may desire: (1) to operate the imaging camera within a narrow opening of a surgical orifice; (2) to adjust the zoom of captured images by manually adjusting the distance between the imaging camera lens and the surgical point of interest 510; or (3) retracting the imaging camera from a narrow opening of the surgical orifice when other surgical instruments may need to be inserted into the narrow opening of the surgical orifice.

Figure 5D:
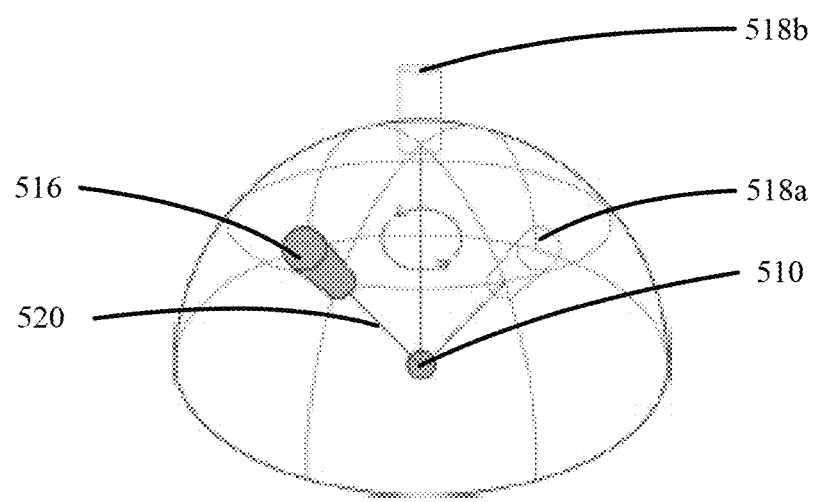

FIG. 5D illustrates the orbit mode described herein. The orbit mode may constrain end effector movement along a surface of a notional spherical volume, where the notional spherical volume may be centered at the surgical point of interest 510. For example, if an imaging camera is affixed to the end effector 316 (FIG. 3) and configured to capture images of the surgical point of interest 510, in the orbit mode, the imaging camera may capture images of the surgical point of interest 510 such that the focus distance between the imaging camera lens and the surgical point of interest 510 remains the same. That is, the imaging camera may change position or orientation for capturing images of the surgical point of interest 510 based on constraints that the imaging camera maintains the focus distance to the surgical point of interest 510.

Figure 6:
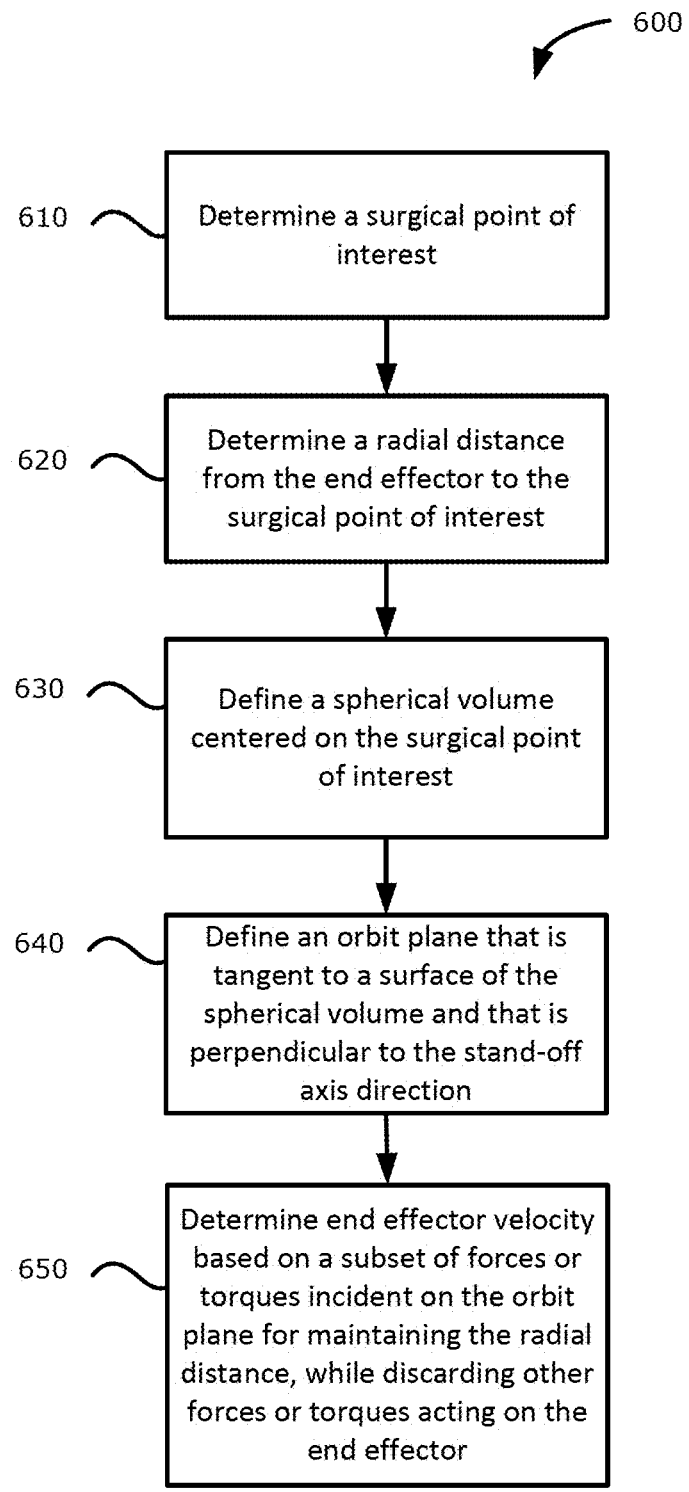
FIG. 6 illustrates, in flowchart form, a method of positioning an end effector when an orbit mode is enabled, in accordance with an embodiment of the present application.

Simultaneous reference is now made to FIG. 6, which illustrates, in flowchart form, a method of positioning the end effector 516 (FIG. 5D) when the surgical mode is the orbit mode. At operation 610, the processor may determine, or identify, the surgical point of interest 510. The surgical point of interest 510 may be an organ or a cluster of tissue on which a surgeon may be conducting a medical procedure. In some examples, the processor 202 may receive, via an input device of the surgical navigation system, input for identifying the surgical point of interest 510 (FIG. 5D). In some other examples, the processor 202 may identify the surgical point of interest 510 based on image recognition methods. In some examples, the processor 202 may identify features currently within the view of the lens as the surgical point of interest 510 and retain identification data of such features in a memory device.

At operation 620, the processor 202 may determine a radial distance from the end effector 516 to the surgical point of interest 510. In some examples, the processor 202 may receive, via an input device of the surgical navigation system, input for determining the radial distance from the end effector 516 to the surgical point of interest 510. That is, the medical professional may define the notional spherical volume for the orbit mode based on a desired radial distance. In some other examples, the processor 202 may determine the radial distance based on a present position of the end effector 516 to the surgical point of interest 510 by using image processing techniques. For example, a depth map may be utilized for determining the radial distance from the end effector 516 to the surgical point of interest 510.

In the orbit mode, an axis of interest 520 of the end effector 516 may intersect the surgical point of interest 510, and the distance between the end effector and the surgical point of interest 510 can remain constant. For example, the axis of interest may be described relative to the task-coordinate space, and the axis of interest may change when the end effector 516 moves within the task-coordinate space. For example, as illustrated in FIG. 5D, when the end effector 516 moves towards a first position 518a, the axis of interest can change. Although the axis of interest within the task-coordinate space may change, the axis of interest can continue to intersect the surgical point of interest 510. Further, when the end effector further moves towards a second position 518b, the axis of interest can further change. Again, although the axis of interest can further change, the axis of interest may continue to intersect the surgical point of interest 510. Accordingly, while in the orbit mode, each respective end effector position may be associated with a different axis of interest. It will be appreciated that in some scenarios, the end effector 516 having a first axis of interest while at a first end effector position may also have that same first axis of interest when the end effector 516 may be positioned at an opposite or opposing side of the notional spherical volume.

Based at least on the surgical point of interest 510 and the determined radial distance from the end effector 516 to the surgical point of interest 510, at operation 630, the processor 202 may define a spherical volume centered on the surgical point of interest 510, as illustrated in FIG. 5D. The notional spherical volume may be used as a reference for constraining movement of the end effector 516 while the positioning arm is in the orbit mode.

At operation 640, the processor 202 may define an orbit plane that is: (1) tangent to a surface of the spherical volume;

and (2) perpendicular to the axis of interest (e.g., axis of interest 520 of FIG. 5D) direction. It may be appreciated that only forces not acting on the orbit plane may contribute to constraining movement of the end effector along the surface of the defined spherical volume that is centered on the surgical point of interest 510.

Thus, while in the orbit mode, at operation 650 (which may correspond to operation 440 of FIG. 4), the processor 202 may be configured to determine the end effector velocity based on a subset of the applied forces incident on the orbit plane and applied torques perpendicular to the orbit plane for maintaining the radial distance, while discarding other forces or torques acting on the end effector 516. That is, when determining the end effector velocity in the orbit mode, the processor 202 may be configured to set to zero the forces or the torques that may cause the end effector 516 to move in a direction that is away from the surface of the notional spherical volume. Forces or torques components that may cause the end effector 516 to increase or decrease the distance between the end effector 516 and the surgical point of interest 510 can be set to zero.

In some embodiments, the processor 202 may set forces or torques causing an end effector to rotate about the axis of interest to zero. For example, the surgical navigation system may be configured to constrain roll movement about the axis of interest. Roll movement about the axis of interest may be challenging to view on a display screen of the surgical navigation system.

In the orbit mode, movements of the end effector 516 off of the surface of the notional spherical volume are constrained by the positioning arm 300 of FIG. 3. Constraining end effector movement to a surface of a notional spherical volume centered on the surgical point of interest 510 may be useful when the medical professional may require multiple perspective views of the surgical point of interest 510, while maintaining the focal distance between the end effector 516 and the surgical point of interest 510. Overall, constraining end effector movement may be useful for limiting opportunities to injure or cause damage to a surgical site by the end effector 516. Constraining end effector movement to specific axis or directions may also be useful for reducing the amount of attention required by a medical professional for adjusting the end effector 516 to a controlled position or orientation.

In another embodiment of the orbit mode, at operation 650, the processor 202 may determine the end effector velocity using an alternate group of operations. In this alternate example, the task-coordinate space may be a spherical coordinate space and spherical coordinates may be relative to the surgical point of interest. The processor 202 may discard torques about the axis of interest direction that are acting on the end effector. For example, when determining the end effector velocity, the processor 202 may set to zero the applied torque about the axis of interest.

At operation 650, the processor 202 may also determine a subset of forces incident on the orbit plane acting on the end effector for maintaining the radial distance. In this example, the subset of forces may be defined the task-coordinate space that is the spherical coordinate space. Accordingly, the processor 202 may determine the force incident on the orbit plane for maintaining the radial distance between the end effector 516 and the surgical point of interest 510. The processor 202 may determine the end effector velocity based on disregarding forces not incident on the orbit plane for maintaining the radial distance.

The description associated with FIGS. 5A, 5B, 5C, and 5D illustrate several examples of surgical modes for the positioning arm 300 of FIG. 3. End effector movement within the task-coordinate space may be constrained based on the surgical mode for the positioning arm 300 of FIG. 3. Further, end effector movement may be determined based on the determined end effector velocity according to the methods described herein. Thus, in response to manipulation of the end effector (e.g., by the medical professional or user of the positioning arm), the end effector may define an updated movement direction in the task-coordinate space. By determining an end effector velocity and generating movement in a direction based on the end effector velocity, the end effector may move based on (1) detected manipulation of the end effector; and (2) constraints to movement based on the surgical mode. An updated position of the end effector is determined when the processor 202 ceases to detect manipulation of the end effector.

For moving the end effector in the task-coordinate space, at operation 450 (FIG. 4), the processor 202 may apply at least one joint space movement in the plurality of joints based on the end effector velocity. As described above, the end effector velocity may cause end effector movement based on: (1) the surgical mode defining movement constraints (e.g., surgical modes described with reference to FIGS. 5A, 5B, 5C, 5D); and/or (2) force or torque after the movement constraints are taken into account.

In some embodiments, the processor 202 may determine joint space movements in the plurality of joints using inverse arm kinematics. Inverse kinematics can be utilized for generating new joint positions based on the determined end effector velocity, where the determined end effector velocity is based on desired end effector movements in the task-coordinate space. For example, the inverse arm kinematics may be associated with a kinematic chain. The kinematic chain may represent the plurality of arm segments connected by respective joints in the plurality of joints. Accordingly, the positioning arm 300 of FIG. 3 may, for example be modeled by the kinematic chain, such that the position and orientation of the end effector 316 (FIG. 3) in the task-coordinate space may be associated with a respective joint position for each joint in the plurality of joints.

When the processor 202 determines the end effector velocity based on the surgical mode and the detected forces or torques acting on the end effector 316, the processor 202 may determine the necessary joint space movement(s) for the plurality of joints for causing movement of the end effector 316 to the updated end effector position. Because the processor 202 may determine, from joint encoders, joint positions of the plurality of joints, the processor 202 may apply joint space movements to the plurality of joints by transmitting joint space parameters to each actuator and/or joint encoders of the plurality of joints.

Embodiments of the present application may utilize inverse arm kinematics for determining at least one joint space movement for the plurality of joints. However, the present application need not be limited to utilizing inverse arm kinematics for determining joint space movements for adjusting the positioning arm described herein. Other methods for determining joint space movements for the positioning arm may be utilized for positioning an end effector that is coupled to the positioning arm of the surgical navigation system.

Figure 7D:
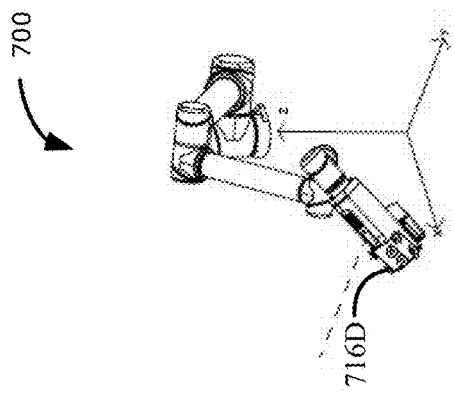
FIGS. 7A, 7B, 7C, and 7D illustrate configurations of a positioning arm while in translate mode, in accordance with an embodiment of the present application.
Figure 7C:
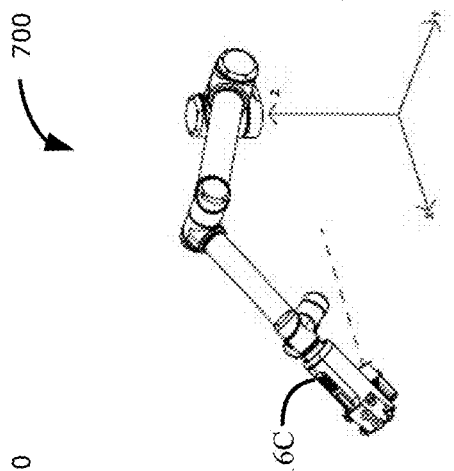
Figure 7B:
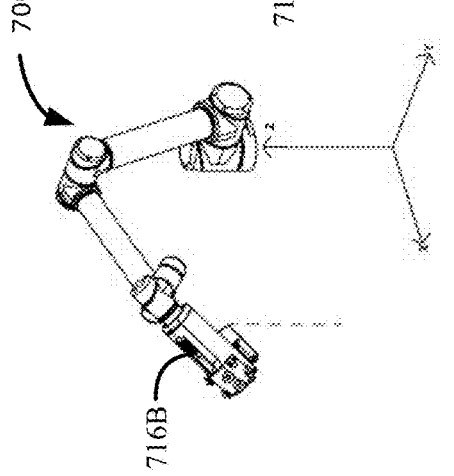
Figure 7A:
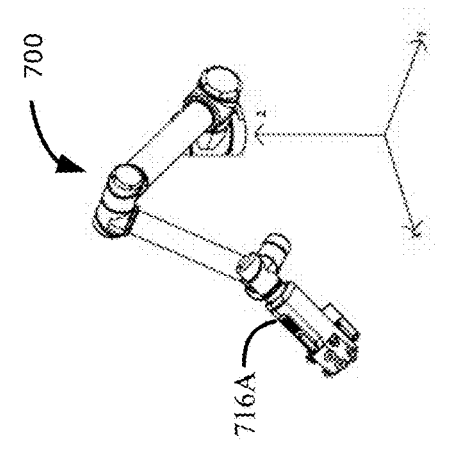

Reference is now made to FIGS. 7A, 7B, 7C, and 7D, which illustrate configurations of a positioning arm 700 while in translate mode. In FIG. 7A, the positioning arm 700 may begin at an initial position, such as a first end effector position 716A in the task-coordinate space. For example, in FIGS. 7A, 7B, 7C, and 7D, the task-coordinate space may be a three dimensional Cartesian coordinate space.

A processor of the positioning arm 700 may implement the example method 400 of FIG. 4 for moving the end effector towards an updated end effector position. When the surgical mode is the translate mode, the processor may determine an end effector velocity based on the detected forces on the end effector, while discarding torques acting on the end effector. The processor may apply at least one joint space movement in the plurality of joints based on the end effector velocity.

For example, in FIG. 7B, the processor may apply at least one joint space movement in the plurality of joints for translating the end effector movement to a second end effector position 716B. As illustrated in FIG. 7B, movement towards the second end effector position 716B may be a result of end effector movement in the z-axis direction (relative to the first end effector position 716A of FIG. 7A).

In FIG. 7C, the processor may apply at least one joint space movement in the plurality of joints for translating the end effector movement to a third end effector position 716C. As illustrated in FIG. 7C, movement towards the third end effector position 716C may be a result of end effector movement in the x-direction (relative to the first end effector position 716A of FIG. 7A).

In FIG. 7D, the processor may apply at least one joint space movement in the plurality of joints for translating the end effector movement to a fourth end effector position 716D. As illustrated in FIG. 716D, movement towards the fourth end effector position 716D may be a result of end effector movement in the y-axis direction (relative to the first end effector position 716A of FIG. 7A).

Although end effector movements in FIGS. 7B, 7C, and 7D, relative to FIG. 7A, are illustrated as movements in one axis, end effector movement in the translate mode may include movements that may include simultaneous movements in two or more axis of the task-coordinate space. In some examples, the at least one joint space movement in the plurality of joints may be based on inverse arm kinematics for positioning the end effector in the various updated end effector positions.

Reference is now made to FIGS. 8A and 8B, which illustrate configurations of the positioning arm 800 while in the stand-off mode. In FIG. 8A, the positioning arm 800 may begin at an initial position, such as a first end effector position 816A in the task-coordinate space.

A processor of the positioning arm 800 may implement the example method 400 of FIG. 4 for moving the end effector towards an updated end effector position. As illustrated in FIGS. 8A and 8B, when the surgical mode is the stand-off mode, the processor may determine a stand-off axis 804 for the end effector. Further, the processor may determine an end effector velocity based on forces acting on the end effector along the stand-off axis 804, while discarding other forces not acting along the stand-off axis and discarding torques acting on the end effector. The processor may apply at least one joint space movement in the plurality of joints based on the end effector velocity.

For example, in FIG. 8B, the processor may apply at least one joint space movement in the plurality of joints for moving the end effector towards a second end effector position 816B. As illustrated in FIG. 8B, the second end effector position 816B may be a result of end effector movement in a downward direction that is along the stand-off axis 804 (relative to the first end effector position 816A of FIG. 8A). In some examples, the at least one joint space movement in the plurality of joints may be based on inverse arm kinematics for positioning the end effector in the updated end effector position along the stand-off axis 804.

Figure 9C:
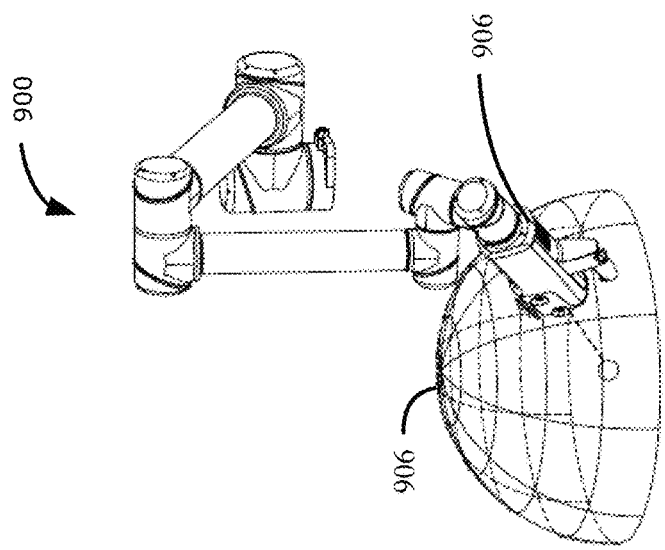
FIGS. 9A, 9B, and 9C illustrate configurations of the positioning arm while in the orbit mode, in accordance with an embodiment of the present application.
Figure 9B:
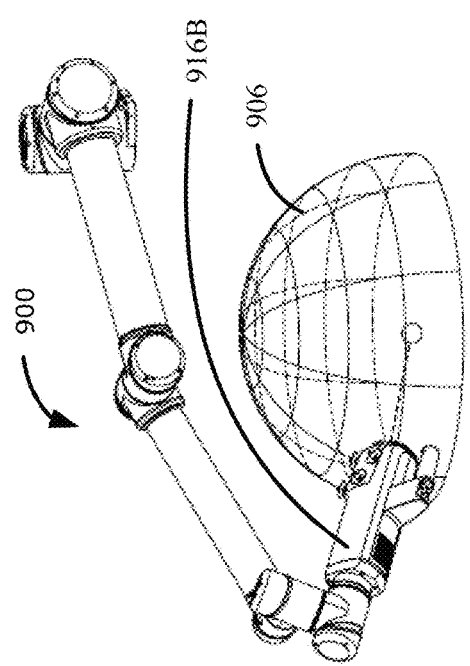
Figure 9A:
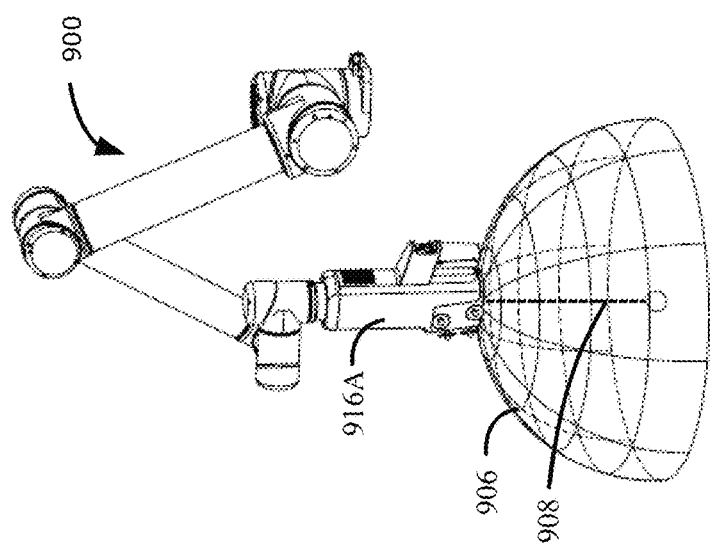

Reference is now made to FIGS. 9A, 9B, and 9C, which illustrate configurations of the positioning arm 900 while in the orbit mode. In FIG. 9A, the positioning arm 900 may begin at an initial position, such as a first end effector position 916A in the task-coordinate space.

A processor of the positioning arm 900 may implement the example method 400 of FIG. 4 for positioning the end effector in an updated end effector position. As illustrated in FIGS. 9A, 9B, and 9C, when the surgical mode is in the orbit mode, the processor may define a notional spherical volume 906 centered on a surgical point of interest based on a radial distance 908. In FIGS. 9A, 9B, and 9C, a hemisphere centered on the surgical point of interest based on the radial distance 908 is illustrated; however, in some embodiments, the positioning arm 900 may move the end effector towards an updated end effector position that may be at any position along a surface of a full notional spherical volume.

The processor of the positioning arm 900 may define an orbit plane (not explicitly illustrated in FIGS. 9A, 9B, 9C) that is tangent to the spherical volume and that is perpendicular to a stand-off axis direction. The processor may further determine the end effector velocity based on a subset of forces or torques incident on the orbit plane for maintaining the radial distance 908, while discarding other forces or torques acting on the end effector.

For example, in FIG. 9B, the processor may apply at least one joint space movement in the plurality of joints of the positioning arm 900 for moving the end effector towards a second end effector position 916B. As illustrated in FIG. 9B, the second end effector position 916B may be a result of end effector movement along the surface of the notional spherical volume 906.

In FIG. 9C, the processor may apply further joint space movements in the plurality of joints of the positioning arm 900 for moving the end effector towards a third end effector position 916C. As illustrated in FIG. 9C, the third end effector position 916C may be a result of further end effector movement along the surface of the notional spherical volume 906.

Figure 10B:
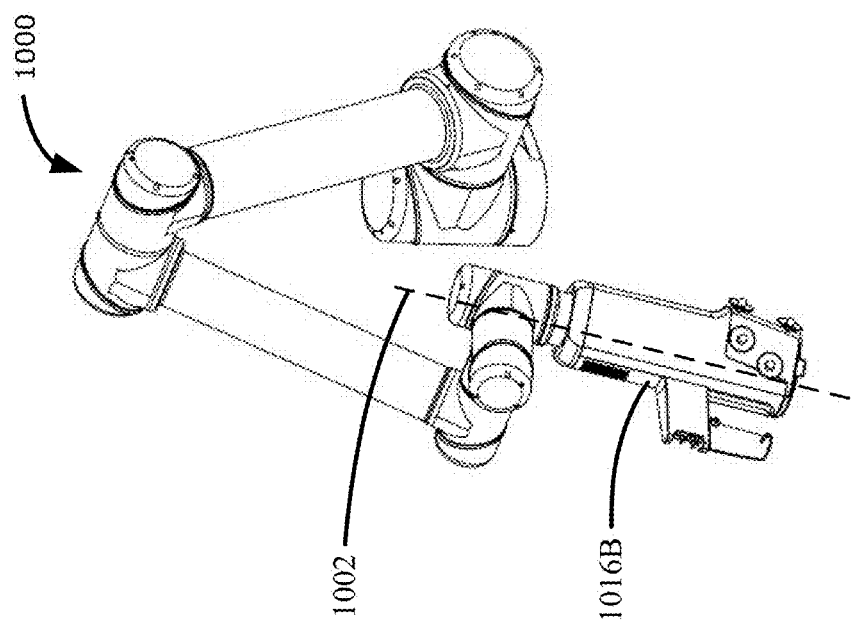
FIGS. 10A and 10B illustrate configurations of the positioning arm while in the roll mode, in accordance with an embodiment of the present application.
Figure 10A:
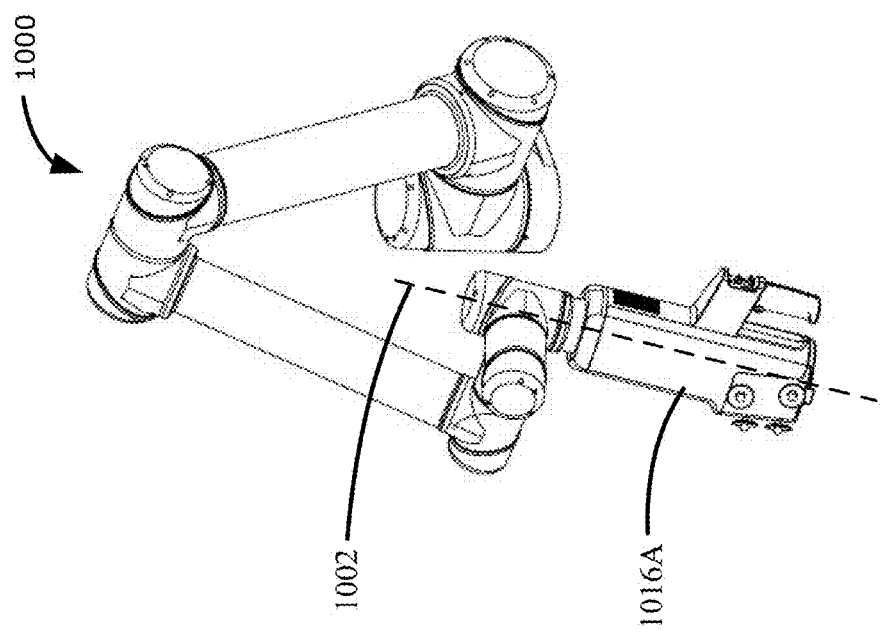

Reference is now made to FIGS. 10A and 10B, which illustrate configurations of the positioning arm 1000 while in the roll mode. In FIG. 10A, the positioning arm 1000 may position the end effector at a first end effector position 1016A in the task-coordinate space.

A processor of the positioning arm 1000 may implement the example method 400 of FIG. 4 for positioning the end effector in an updated end effector position. As illustrated in FIGS. 10A and 10B, the processor may determine a roll axis 1002 for the end effector. As illustrated in FIGS. 10A and 10B, the roll axis 1002 may be an axis adjoining a surgical point of interest and an end tip of the end effector. For example, the roll axis 1002 may be an axis through a longitudinal center of the end effector and that may intersect a surgical point of interest. Further, the processor may determine a roll torque about the roll axis from the determined forces or torques acting on the end effector. The processor may determine the end effector velocity based on the roll torque acting on the end effector, while discarding other forces or torques of the determined forces or torques acting on the end effector. The processor may apply at least one joint space movement in the plurality of joints based on the end effector velocity.

For example, the processor may apply the at least one joint space movement for moving the end effector towards a second end effector position 1016B. As illustrated in FIG. 10B, the second end effector position 1016B may be a result of a rotation of the end effector. In FIG. 10B, the end effector handle has been rotated towards the second end effector position 1016B. For example, the end effector handle has been rotated by a revolving joint at a second arm end of the positioning arm, while other joint positions may not have changed (e.g., compare FIG. 10A to FIG. 10B). In some examples, the joint space movement for rotating the end effector from the first end effector position 1016A towards the second end effector position 1016B may be based on inverse arm kinematics for positioning the end effector in the updated end effector position about the roll axis 1002.

As described and illustrated in various drawings herein, based on a surgical mode of the positioning arm, movement constraints may be applied for determining an end effector velocity. An end effector velocity may be used for defining an updated end effector position in the task-coordinate space. At least one joint space movement in the plurality of joints of a positioning arm may be based on inverse arm kinematics for positioning the end effector in the updated end effector position within the task-coordinate space.

Figure 11C:
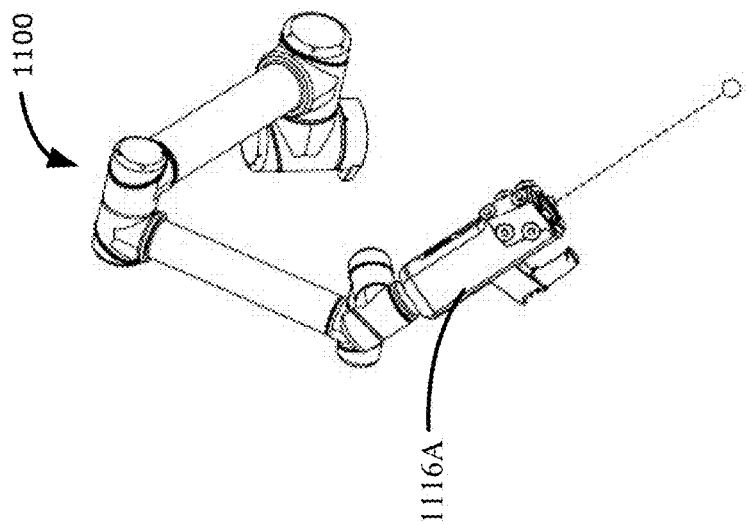
FIGS. 11A, 11B, and 11C illustrate configurations of the positioning arm subject to a memory mode, in accordance with an embodiment of the present application.
Figure 11B:
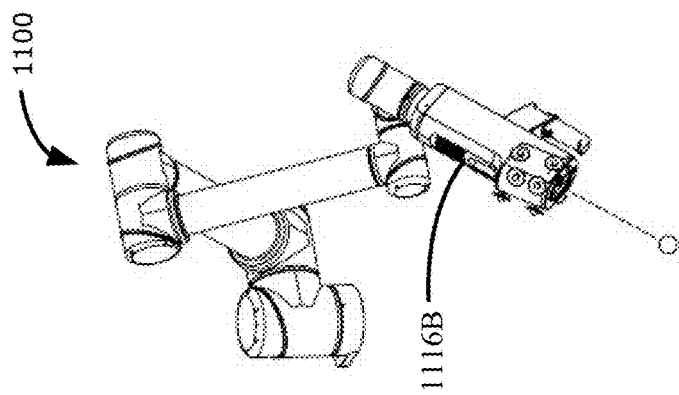
Figure 11A:
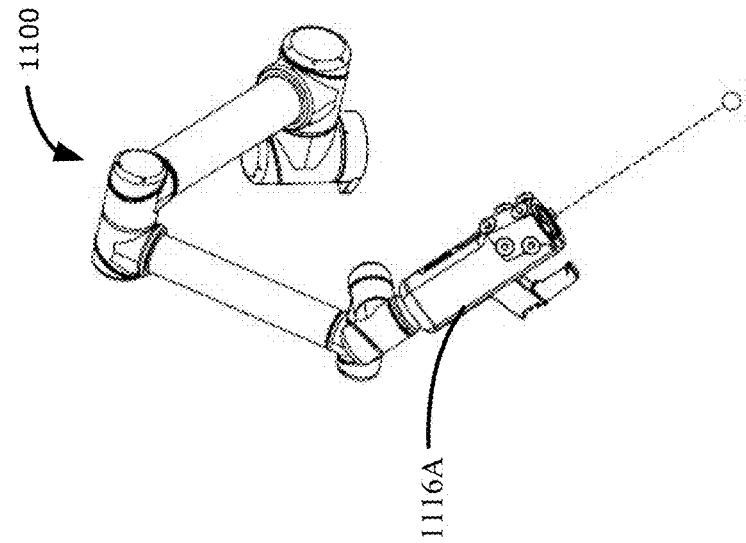

Reference is now made to FIGS. 11A, 11B, and 11C, which illustrate configurations of the positioning arm 1100 subject to a memory mode, in accordance to embodiments of the present application. In FIG. 11A, the positioning arm 1100 may position the end effector at a first end effector position 1116A in the task-coordinate space. The position of the end effector at the first end effector position 1116A in the task-coordinate space may be stored by the positioning arm 1100 in memory. As will be described, the first end effector position 1116A may be recalled when the surgical mode is a memory mode.

In FIG. 11B, the positioning arm 1100 may move the end effector towards a second end effector position 1116B in the task-coordinate space. Compared to the first end effector position 1116A illustrated in FIG. 11A, the second end effector position 1116B may be positioned to be at a different position and/or orientation in the task-coordinate space. Further, the end effector in the second end effector position 1116B may be at a different distance from a surgical point of interest than that of the first end effector position 1116A. In some examples, the surgical point of interest in FIG. 11B may be different than that in FIG. 11A.

When the surgical mode is a memory mode, the processor may determine an end effector velocity for moving the end effector towards the end effector position stored in memory, such as the first end effector position 1116A. Accordingly, when the surgical mode is the memory mode, the processor may apply at least one joint space movement in the plurality of joints based on the end effector velocity to return the end effector to the first end effector position 1116A, as illustrated in FIG. 11C. That is, the configuration of the positioning arm 1100 and the position and orientation of the end effector in FIG. 11A is the same as that in FIG. 11C. Accordingly, with the memory mode, the positioning arm 1100 may save joint positions of each joint in the plurality of joints, such that the position of the end effector in the task-coordinate space may be retrieved at a later time. When in memory mode, the processor may determine an end effector velocity for returning the positioning arm 1100 to saved joint positions, such that the end effector may return to a first end effector position 1116A.

Certain adaptations and modifications of the described embodiments can be made. Therefore, the above discussed embodiments are considered to be illustrative and not restrictive.

What is claimed is:

1. A motion-assisted positioning arm for a medical procedure, the positioning arm comprising:
a base;
an arm configured to couple with the base, the arm having a first arm end and a second arm end, and the arm comprising:
a plurality of arm segments extending from the first arm end to the second arm end;
a plurality of joints, each joint of the plurality of joints configured to couple each arm segment with another arm segment; and
an end effector configured to couple with the second arm end, wherein the end effector is manipulable with six degrees of freedom in a task-coordinate space based on motion by at least one joint of the plurality of joints;
a processor operably coupled with the plurality of joints and the end effector, the processor configured by processor-readable instructions storable in relation to a memory to:
determine a memory mode for returning the end effector to a saved position by constraining movement of the end effector in the task-coordinate space;
determine a surgical mode for constraining movement of the end effector in the task-coordinate space, the surgical mode defining an updated end effector position in the task-coordinate space;
determine an end effector velocity based on the memory mode, the surgical mode, at least one of forces and torques on the end effector, and at least one of a subset of the forces and a subset of torques on the end effector while disregarding at least one of remaining forces and remaining torques on the end effector; and
instruct movement in space of at least one joint of the plurality of joints based on the end effector velocity.

2. The positioning arm of claim 1, wherein the saved position of the end effector comprises joint positions of each joint of the plurality of joints.

3. The positioning arm of claim 1, wherein the processor is further configured, by the processor-readable instructions, to:
prior to determining the end effector velocity, recall the saved end effector position from the memory; and
determine the end effector velocity by further disregarding at least one of other forces and other torques on the end effector.

4. The positioning arm of claim 1, wherein the end effector comprises a force-moment sensor for determining at least one of the forces and the torques on the end effector.

5. The positioning arm of claim 1, wherein each joint of the plurality of joints comprises an actuator for facilitating movement.

6. The positioning arm of claim 1, wherein each joint of the plurality of joints comprises a joint encoder for determining a joint position.

7. The positioning arm of claim 6, wherein the joint position comprises an angular position.

8. The positioning arm of claim 1, wherein the processor is further configured, by the processor-readable instructions, to determine the movement of the at least one joint by using inverse arm kinematics for moving the end effector in the task-coordinate space.

9. The positioning arm of claim 1, wherein the end effector is configured to receive at least one of: at least one imaging device and a surgical tool.

10. The positioning arm of claim 9, wherein the end effector is configured to receive the at least one imaging device having fixed focal length lenses.

11. The positioning arm of claim 1, wherein the processor is further configured, by the processor-readable instructions, to determine at least one of the memory mode and the surgical mode based on input from an input interface.

12. The positioning arm of claim 1, wherein the task coordinate space comprises a three-dimensional Cartesian coordinate space.

13. The positioning arm of claim 1, wherein the end effector velocity comprises a magnitude and a direction.

14. The positioning arm of claim 1, wherein the end effector comprises an end effector engagement switch to enable detection of end effector manipulation.

15. The positioning arm of claim 1, wherein the medical procedure comprises at least one of: surgical navigation, robotic surgery, robotically-assisted surgery, an ophthalmology procedure, and an endoscopy procedure.

16. The positioning arm of claim 1, wherein the processor is configured to interface with at least one of an external device and a peripheral device.

17. The positioning arm of claim 16, wherein the processor is configured to interface with a tracking detector to track at least one of the position, an orientation, and the movement of the end effector.

18. The positioning arm of claim 17, wherein the end effector comprises at least one affixed fiducial marker, and wherein the tracking detector is configured to track at least one of the position, the orientation, and the movement of the end effector in the task coordinate space.

19. The positioning arm of claim 16, wherein the memory comprises at least one of a local device and a remote memory device.

20. The positioning arm of claim 1, wherein the processor is further configured to determine the surgical mode based on input from an input interface, and wherein the surgical mode comprises at least one of a free motion mode, a roll mode, a translate mode, a stand-off mode, and an orbit mode.

* * * * *